(12) United States Patent
Kamijo

(10) Patent No.: US 9,426,999 B2
(45) Date of Patent: Aug. 30, 2016

(54) METHOD FOR CULTURING LACTIC ACID BACTERIUM AND METHOD FOR PRODUCING FERMENTED MILK

(75) Inventor: Masayuki Kamijo, Odawara (JP)

(73) Assignee: MEIJI CO., LTD., Tokyo (JP)

( * ) Notice: Subject to any disclaimer, the term of this patent is extended or adjusted under 35 U.S.C. 154(b) by 0 days.

(21) Appl. No.: 13/260,249

(22) PCT Filed: Mar. 26, 2010

(86) PCT No.: PCT/JP2010/055440
§ 371 (c)(1),
(2), (4) Date: Sep. 23, 2011

(87) PCT Pub. No.: WO2010/113816
PCT Pub. Date: Oct. 7, 2010

(65) Prior Publication Data
US 2012/0015073 A1    Jan. 19, 2012

(30) Foreign Application Priority Data
Mar. 30, 2009   (JP) ................. 2009-081841

(51) Int. Cl.
*C12P 7/56* (2006.01)
*C12N 1/20* (2006.01)
*A23C 9/123* (2006.01)

(52) U.S. Cl.
CPC ............ *A23C 9/1234* (2013.01); *C12N 1/20* (2013.01); *A23Y 2220/00* (2013.01); *A23Y 2220/37* (2013.01); *A23Y 2300/41* (2013.01)

(58) Field of Classification Search
None
See application file for complete search history.

(56) References Cited

U.S. PATENT DOCUMENTS

| | | | |
|---|---|---|---|
| 4,115,199 A * | 9/1978 | Porubcan et al. | ......... 435/252.4 |
| 4,771,001 A * | 9/1988 | Bailey et al. | ................. 435/139 |
| 5,173,297 A | 12/1992 | Vedamuthu et al. | |
| 5,378,458 A * | 1/1995 | Mayra-Makinen et al. | . 424/93.3 |
| 5,445,835 A * | 8/1995 | Vedamuthu | .......... A23C 9/1585 426/42 |
| 6,010,725 A | 1/2000 | Meister et al. | |
| 7,776,370 B2 * | 8/2010 | Dias et al. | ....................... 426/43 |
| 2009/0306210 A1 | 12/2009 | Behnam | |
| 2011/0129568 A1 | 6/2011 | Fukui et al. | |

FOREIGN PATENT DOCUMENTS

| JP | 6-009690 A | 1/1994 |
|---|---|---|
| JP | 8-187071 A | 7/1996 |
| JP | 8-187072 A | 7/1996 |
| JP | 10-057031 A | 3/1998 |
| JP | 2002-369672 A | 12/2002 |
| JP | 2003-235529 A | 8/2003 |
| JP | 2004-283109 A | 10/2004 |
| JP | 2005-080636 A | 3/2005 |
| JP | 2006-238833 A | 9/2006 |
| JP | 2008-005834 A | 1/2008 |
| WO | WO-2007-101495 A1 | 9/2007 |
| WO | WO-2007-138993 A1 | 12/2007 |
| WO | WO 2007138993 A1 * | 12/2007 |
| WO | WO 2008016214 A1 * | 2/2008 |
| WO | WO-2010-001580 A1 | 1/2010 |

OTHER PUBLICATIONS

De Man, JC, Rogosa, M, and Sharpe, ME, "A Medium for the Cultivation of Lactobacilli", Journal of Applied Bacteriology 1960, vol. 23, Issue 1, pp. 130-135.*

Hutkins, RW. "Starter Cultures", In Microbiology and Technology of Fermented Foods, Wiley Online Library, published online on Nov. 2007; Chapter 3, p. 84.*

Maqueda, M., Sanchez-Hidalgo, M., Fernandez, M., Montalban-Lopez, M., Valdivia, E., and Martinez-Buena M. "Genetic features of circular bacteriocins produced by Gram-positive bacteria", FEMS Microbiol Rev, EPub 2007, vol. 32, pp. 2-22.*

Bromberg, R., Moreno, I., Zaganini, C.L., Delboni, R.R., and de Oliveira, J. "Isolation of Bacteriocin-Producing Lactic Acid Bacteria From Meat and Meat Products and Its Spectrum of Inhibitory Activity", Brazilian Journal of Microbiology 2004, vol. 35, pp. 137-144.*

Zhu et al., "Isolation and characterization of a new bacteriocin from Lactobacillus gasseri KT7", Journal of Applied Microbiology 2000, vol. 88, pp. 877-886.*

Peter M. Muriana et al., "Conjugal Transfer of Plasmid-Encoded Determinants for Bacteriocin Production and Immunity in Lactobacillus acidophilus 88", Applied and Environmental Microbiology, Mar. 1987, pp. 553-560.

(Continued)

*Primary Examiner* — Renee Claytor
*Assistant Examiner* — Michelle F Paguio Frising
(74) *Attorney, Agent, or Firm* — Rabin & Berdo, P.C.

(57) ABSTRACT

First, prepared is a whey degradation medium to which a protease, yeast extract, and the like are added. Further, polyoxyethylene sorbitan monooleate or propylene glycol monooleate is added to the whey degradation medium. The whey degradation medium is inoculated with bacteriocin-producing lactic acid bacterium and the lactic acid bacterium is cultured while the whey degradation medium is maintained at pH of 4 to 5. After the completion of the culture, the whey degradation medium (culture solution) is centrifuged to thereby separate therefrom a concentrated cell suspension containing the lactic acid bacterium in a concentrated form. The concentrated cell suspension has very low antibacterial activity (several tens AU or less). Then, by adding the concentrated cell suspension to a yogurt mix and fermenting the same, it is possible to produce yogurt containing the bacteriocin-producing lactic acid bacterium without any delay in the fermentation.

13 Claims, 3 Drawing Sheets

(56) References Cited

OTHER PUBLICATIONS

Svetoslav D. Todorov et al., "Effect of Growth Medium on Bacteriocin Production by Lactobacillus plantarum ST194BZ, a Strain Isolated from Boza", Food Technol. Biotechnol. 43(2), 2005, pp. 165-173.

Simone, Hickmann, Flores: "Nisin Production from Lactococcus lactis A.T.C.C. 7962 using supplemented whey permeate", Biotechnol. Appl. Biochem., Jan. 1, 2001, pp. 103-107.

George A. Somkuti et al.: "Influence of Organic Buffers on Bacteriocin Production by *Streptococcus thermophilus* ST110", Current Microbiology, Springer-Verlag, NE, vol. 55, No. 2, Jul. 11, 2007, pp. 173-177.

Shimizu. H. et al.: "Nisin Production by a Mixed-Culture System Consisting of Lactococcus lactis and Kluyveromyces marxianus", Applied and Environmental Microbiology, American Society for Microbiology, US, vol. 65, No. 7, Jul. 1, 1999, pp. 3134-3141.

Amiali M. N. et al.: "High raisin Z production by Lactococcus lactis UL719 in whey permeate with aeration", World Journal of Microbiology and Biotechnology, Rapid Communications of Oxford, Oxford, GB, vol. 14, Jan. 1, 1998, pp. 887-894.

Georgalaki M. D. et al.: "Macedocin, a food-grade lantibiotic produced by *Streptococcus macedonicus* ACA-DD 198", Applied and Environmental Microbiology, American Society for Microbiology, US, vol. 68, No. 12, Dec. 20, 2002, pp. 5891-5903.

Parente et al.: "A comparison of factors affecting the production of two bacteriocins from lactic acid bacteria," Journal of Applied Bacteriology, vol. 73, 1992, pp. 290-298.

Huot et al.: "Tween 80 effect on bacteriocin synthesis by *Lactococcus lactis* subsp. *cremoris* J46," Letters in Applied Microbiology, vol. 22, 1996, pp. 307-310.

Bhatti et al.: "Factors affecting the antilisterial effects of nisin in milk," International Journal of Food Microbiology, vol. 97, 2004, pp. 215-219.

Itoh et al.: "Inhibition of food-borne pathoenic bacteria by bacteriocins from Lactobacillus gasseri," Letters in Applied Microbiology, vol. 21, 1995, pp. 137-141.

\* cited by examiner

Fig. 1

COMPOSITION OF WHEY DEGRADATION MEDIUM (EXAMPLE 1)

| RAW MATERIAL | BLEND RATIO [WT%] | |
| --- | --- | --- |
| | BLEND A | BLEND B |
| WHEY POWDER | 8.70 | 8.70 |
| WHEY PROTEIN CONCENTRATE (WPC80) | 1.50 | 1.50 |
| PROTEASE A "AMANO" G | 0.10 | 0.10 |
| BREWER'S YEAST EXTRACT (MEAST) | 0.20 | 0.20 |
| FISH EXTRACT (TUNA, OCEANIC BONITO) | 0.50 | 0.50 |
| SODIUM ASCORBATE Na | 0.10 | 0.10 |
| FERROUS SULFATE | 0.05 | 0.05 |
| EMULSIFIER (POLYSORBATE 80) | 0.05 | |
| EMULSIFIER (SUN SOFT 81S) | | 0.05 |
| WATER | 88.80 | 88.80 |

Fig. 2

RESULT OF CULTURE OF LACTOBACILLUS GASSERI OLL2959 (EXAMPLE 1)

| | VIABLE CELL COUNT (cfu/ml) | ANTIBACTERIAL ACTIVITY (AU/ml) | ANTIBACTERIAL ACTIVITY (AU/1×$10^9$cfu) |
| --- | --- | --- | --- |
| BLEND A | 1.1×$10^{10}$ | LOWER THAN 200 | LOWER THAN 20 |
| BLEND B | 1.6×$10^{10}$ | 18000 | 1100 |

Fig. 3

COMPOSITION OF WHEY DEGRADATION MEDIUM (EXAMPLE 2)

| RAW MATERIAL | BLEND RATIO [WT%] | |
| --- | --- | --- |
| | BLEND C | BLEND D |
| WHEY POWDER | 8.70 | 8.70 |
| WHEY PROTEIN CONCENTRATE (WPC80) | 1.50 | 1.50 |
| PROTEASE A "AMANO" G | 0.10 | 0.10 |
| BREWER'S YEAST EXTRACT (MEAST) | 0.20 | 0.20 |
| FISH EXTRACT (TUNA, OCEANIC BONITO) | 0.50 | 0.50 |
| SODIUM ASCORBATE Na | 0.10 | 0.10 |
| FERROUS SULFATE | 0.05 | 0.05 |
| EMULSIFIER (POLYSORBATE 80) | 0.025 | |
| EMULSIFIER (SUN SOFT 81S) | 0.025 | |
| EMULSIFIER (SUN SOFT No. 25) | | 0.05 |
| WATER | 88.80 | 88.80 |

Fig. 4

RESULT OF CULTURE OF LACTOBACILLUS GASSERI OLL2959 (EXAMPLE 2)

| | VIABLE CELL COUNT (cfu/ml) | ANTIBACTERIAL ACTIVITY (AU/ml) | ANTIBACTERIAL ACTIVITY (AU/$1 \times 10^9$ cfu) |
| --- | --- | --- | --- |
| BLEND C | $1.6 \times 10^{10}$ | LOWER THAN 200 | LOWER THAN 15 |
| BLEND D | $1.7 \times 10^{10}$ | LOWER THAN 200 | LOWER THAN 15 |

Fig. 5

COMPOSITION OF YOGURT MIX (RAW MATERIAL MILK) (EXAMPLE 3)

| RAW MATERIAL | BLEND RATIO [WT%] | | | |
|---|---|---|---|---|
| | BLEND E | BLEND F | BLEND G | BLEND H |
| SKIMMED MILK POWDER | 14.10 | 14.10 | 14.10 | 14.10 |
| UNSALTED BUTTER | 0.93 | 0.93 | 0.93 | 0.93 |
| STARTER (MEIJI BULGARIA YOGURT) | 2.00 | 2.00 | 2.00 | 2.00 |
| CONCENTRATED CELL SUSPENSION A (OLL2959) | | 0.10 | | |
| CONCENTRATED CELL SUSPENSION B (OLL2959) | | | 0.10 | |
| CONCENTRATED CELL SUSPENSION C (OLL2959) | | | | 0.10 |
| WATER | 82.97 | 82.87 | 82.87 | 82.87 |

METHOD FOR CULTURING LACTIC ACID BACTERIUM AND METHOD FOR PRODUCING FERMENTED MILK

TECHNICAL FIELD

The present invention relates to a method for culturing bacteriocin-producing lactic acid bacterium and a method for producing fermented milk containing the bacteriocin-producing lactic acid bacterium.

BACKGROUND ART

Fermented milk such as yogurt is produced by adding a starter to raw material milk (yogurt mix) into which raw milk, skimmed milk powder, whey protein, or the like are mixed and fermenting the yogurt mix. As the starter, used is lactic acid bacterium such as *Lactobacillus bulgaricus, Streptococcus thermophilus*, or the like.

It is well known that some kinds of lactic acid bacterium produce an antibacterial protein or peptide called a bacteriocin. As shown in the following Patent Documents 1 and 2, it is possible to improve the preservative quality of foods and give good flavor (taste) to foods by using the bacteriocin-producing lactic acid bacterium.

In the invention of Patent Document 1, *Bifidobacterium* and *Lactococcus lactis* are cocultured by using a liquid culture medium of which the main ingredients are milk and milk constituents. The *Lactococcus lactis* is a type of bacteriocin-producing lactic acid bacterium. By adding the culture solution after the coculture to foods (bread, Udon noodles (Japanese noodles), or the like) as a food preservative, it is possible to improve the preservative quality of the foods and give good flavor to the foods.

Patent Document 2 shows a flavor improving agent obtained by culturing *Lactococcus lactis* with a whey medium to which yeast extract or the like is added and removing the *Lactococcus lactis* from the whey medium after the culture. By using this flavor improving agent, it is possible to get rid of the fishiness of the fish (the fish odor) and give good flavor (taste) to foods.

There is another type of lactic acid bacterium having a function of probiotics which produces beneficial effects on human body when taken in the body, and yogurt using such lactic acid bacterium is in practical use.

[Patent Document 1] Japanese Patent Application Laid Open Gazette No. 8-187071

[Patent Document 2] Japanese Patent Application Laid Open Gazette No. 2004-283109

Some of the lactic acid bacterium having a function of probiotics produce a bacteriocin. For this reason, when yogurt containing the bacteriocin-producing lactic acid bacterium for the purpose of using the function of the probiotics, there sometimes arises a delay in the fermentation of the yogurt mix.

In a process of producing yogurt containing the bacteriocin-producing lactic acid bacterium, a culture of the lactic acid bacterium is inoculated into the yogurt mix. Since the culture contains the bacteriocin produced by the lactic acid bacterium, in the process of producing yogurt, not only the lactic acid bacterium to be used as probiotics but also the bacteriocin is added to the yogurt mix.

The bacteriocin added to the yogurt mix retards the action of the starter, and this delays formation of curds or the like, thereby causing a delay in the fermentation. Therefore, when the culture of the bacteriocin-producing lactic acid bacterium is added to the yogurt mix for the purpose of using the function of the probiotics, it is desirable that the antibacterial activity of the culture should be made as low as possible.

DISCLOSURE OF INVENTION

The present invention is intended for a method for culturing lactic acid bacterium. According to the present invention, the method for culturing lactic acid bacterium comprises a culture solution preparation step of preparing a culture solution containing whey degraded by a proteolytic enzyme, and a culture step of inoculating bacteriocin-producing lactic acid bacterium into the culture solution and culturing the lactic acid bacterium while maintaining the culture solution inoculated with the lactic acid bacterium at pH of not lower than 4 and lower than 5.

By the method for culturing lactic acid bacterium according to the present invention, it is possible to make the antibacterial activity of the culture of the bacteriocin-producing lactic acid bacterium as low as possible.

The present invention is also intended for a method for producing fermented milk. According to the present invention, the method for producing fermented milk comprises a raw material milk producing step of producing a yogurt mix, a culture producing step of culturing a bacteriocin producer which is bacteriocin-producing lactic acid bacterium to thereby produce a culture of the bacteriocin producer, an addition step of adding the culture to the yogurt mix, and a fermentation step of fermenting the yogurt mix to which the culture is added, and in the method of the present invention, the culture producing step includes a culture solution preparation step of preparing a culture solution containing whey degraded by a proteolytic enzyme, and a culture step of inoculating the bacteriocin producer into the culture solution and culturing the bacteriocin producer while maintaining the culture solution inoculated with the bacteriocin producer at pH of not lower than 4 and lower than 5, to thereby produce the culture.

By the method for producing fermented milk according to the present invention, it is possible to prevent the action of the starter in the yogurt mix from being retarded by the bacteriocin. Therefore, the fermented milk containing the bacteriocin producer can be produced with high efficiency.

Therefore, it is an object of the present invention to provide a method for culturing lactic acid bacterium by which a culture with low antibacterial activity can be obtained and a method for producing fermented milk by which any delay in fermentation can be prevented.

These and other objects, features, aspects and advantages of the present invention will become more apparent from the following detailed description of the present invention when taken in conjunction with the accompanying drawings.

BRIEF DESCRIPTION OF DRAWINGS

FIG. 1 is a view showing the respective compositions of whey degradation media used in Example 1;

FIG. 2 is a view showing a result of the culture of *Lactobacillus gasseri* in Example 1;

FIG. 3 is a view showing the respective compositions of whey degradation media used in Example 2;

FIG. 4 is a view showing a result of the culture of *Lactobacillus gasseri* in Example 2; and FIG. 5 is a view showing the respective compositions of yogurt mixes used in Example 3.

BEST MODE FOR CARRYING OUT THE INVENTION

Hereinafter, the preferred embodiment of the present invention will be discussed. In a method for culturing lactic acid bacterium in accordance with the preferred embodiment, lactic acid bacterium is cultured while an alkaline solution is being added to a culture medium so that the pH of the culture medium can be maintained within a certain range (not lower than 4 and lower than 5). It is thereby possible to obtain a culture of the lactic acid bacterium having very low antibacterial activity per viable cell count.

In a method for culturing lactic acid bacterium in accordance with this preferred embodiment, the lactic acid bacterium to be cultured is bacteriocin-producing lactic acid bacterium (hereinafter, referred to as "a bacteriocin producer"). The lactic acid bacterium which belongs to *Lactobacillus* such as *Lactobacillus gasseri*, the lactic acid bacterium which belongs to *Lactococcus* such as *Lactococcus lactis*, and the like can be cultured by using the method for culturing lactic acid bacterium in accordance with this preferred embodiment. Specifically, the lactic acid bacterium includes, for example, *Lactobacillus gasseri* OLL2959 (NITE BP-224, NITE Patent Microorganisms Depositary (NPMD)), *Lactococcus lactis* OLS3311 (FERM BP-10966, International Patent Organism Depositary (IPOD)), *Lactococcus lactis* subsp. *cremoris* OLS3312 (FERM BP-10967, International Patent Organism Depositary (IPOD)), and the like.

Herein, specific discussion will be made on the method for culturing lactic acid bacterium in accordance with this preferred embodiment. First, a proteolytic enzyme such as a protease is added to an aqueous whey solution containing whey, to thereby degrade whey protein in the aqueous whey solution. Before adding the proteolytic enzyme, whey protein such as a Whey Protein Concentrate (WPC), a Whey Protein Isolate (WPI), or the like may be added to the aqueous whey solution.

Next, yeast extract such as brewer's yeast extract is added to the aqueous whey solution, to thereby prepare a whey degradation medium to be used for the culture of the bacteriocin producer. To the whey degradation medium, meat extract, fish extract, or the like besides the whey protein may be added as a nitrogen source. Further, to the whey degradation medium, vitamin such as sodium ascorbate and an inorganic nutrient such as ferrous sulfate, magnesium sulfate, or the like may be added.

Preferably, an emulsifier such as polyoxyethylene sorbitan monooleate, propylene glycol monooleate, or the like may be added to the whey degradation medium. It is thereby possible to reliably suppress the antibacterial activity of the culture of the bacteriocin producer.

The bacteriocin producer is inoculated into the whey degradation medium, to thereby culture the bacteriocin producer. Preferably, the bacteriocin producer is cultured until the pH of the whey degradation medium becomes lower than 5 and then the bacteriocin producer continues to be cultured while the pH of the whey degradation medium in which the bacteriocin producer is cultured is controlled to be in a range of not lower than 4 and lower than 5. The pH can be controlled by adding an alkaline solution to the whey degradation medium. As the alkaline solution, an aqueous potassium carbonate solution, an aqueous sodium hydrogen carbonate solution, or the like may be used. More preferably, the bacteriocin producer is cultured while the pH of the whey degradation medium is controlled to be in a range of not lower than 4.7 and lower than 5. In a case where the pH of the whey degradation medium during the culture is controlled to be in a range of not lower than 4.7 and lower than 5, the growth of the bacteriocin producer is stimulated and the bacteriocin producer can be thereby cultured with high efficiency as compared with the case where the pH of the whey degradation medium during the culture is controlled to be lower than 4.7.

After culturing the bacteriocin producer, a concentrated cell suspension containing the bacteriocin producer in a concentrated form is separated from the whey degradation medium (culture solution) in which the bacteriocin producer is cultured. The concentrated cell suspension can be separated by centrifugal separation or membrane separation.

The concentrated cell suspension of the bacteriocin producer which is thus obtained has antibacterial activity much lower than that of the concentrated cell suspension which is prepared while the pH of the whey degradation medium is controlled to be not lower than 5 during the culture. In other words, by culturing the bacteriocin producer while maintaining the whey degradation medium at pH ranging from 4 to 5, it is possible to control the antibacterial activity of the culture of the bacteriocin producer to be low.

Next, specific discussion will be made on the method for producing fermented milk (yogurt) in accordance with this preferred embodiment. First, a yogurt mix which is raw material milk is prepared. The yogurt mix can be prepared by mixing skimmed milk powder, whey protein, water, and the like into raw milk. Further, sugar, fruit flesh, fruit juice, or the like may be added to the yogurt mix.

After homogenizing and disinfecting the yogurt mix in the same manner as conventionally done, the yogurt mix is inoculated with a starter, the bacteriocin producer obtained by the above-discussed method for culturing lactic acid bacterium, and the concentrated cell suspension thereof. The amount of bacteriocin producer and concentrated cell suspension thereof to be inoculated is not particularly limited.

The lactic acid bacterium to be used as the starter may be the same lactic acid bacterium as the bacteriocin producer or different one.

The yogurt mix inoculated with the bacteriocin producer and the concentrated cell suspension thereof is fermented, to thereby produce yogurt. Since the antibacterial activity of the concentrated cell suspension or the like prepared by the method for producing fermented milk is very low, the action of the starter (lactic acid bacterium) is not retarded during the fermentation of the yogurt mix. Therefore, it is possible to produce yogurt containing the bacteriocin producer with high efficiency in almost the same time for fermentation as in the conventional case.

EXAMPLES

Hereinafter, with reference to figures, discussion will be made on Examples of the method for culturing lactic acid bacterium in accordance with the present invention.

Example 1

FIG. 1 is a view showing the respective compositions of whey degradation media used in Example 1. First, discussion will be made on preparation of the whey degradation medium of Blend A and that of Blend B. Specifically, an aqueous whey solution is prepared by mixing 8.70% by weight of whey powder (manufactured by Meiji Dairies Corporation), 1.50% by weight of Whey Protein Concentrate (WPC80, manufactured by New Zealand Milk Products Co., Ltd.), and 88.80% by weight of water, based on the total weight of each of the whey degradation media of Blends A and B. Then, whey protein in the aqueous whey solution is degraded by adding 0.10% by weight of the proteolytic enzyme (Protease A "Amano" G, manufactured by Amano Enzyme Inc.) to the aqueous whey solution.

After that, 0.20% by weight of brewer's yeast extract (manufactured by Asahi Breweries, Ltd.), 0.50% by weight of fish extract (manufactured by Maruha Nichiro Foods, Inc.), 0.10% by weight of sodium ascorbate, and 0.05% by weight of ferrous sulfate ($FeSO_4$) are added to the aqueous whey solution in which the whey protein is degraded.

Further, 0.05% by weight of Polysorbate 80 (Polyoxyethylene Sorbitan Monooleate, manufactured by NOF CORPORATION) is added as an emulsifier to the aqueous whey solution, to thereby prepare the whey degradation medium of Blend A. Similarly, 0.05% by weight of Sun Soft 81S (Sorbitan Monooleate, manufactured by Taiyo Kagaku Co., Ltd.) is added as an emulsifier to the aqueous whey solution, to thereby prepare the whey degradation medium of Blend B.

Next, Lactobacillus gasseri OLL2959 (NITE BP-224, NITE Patent Microorganisms Depositary (NPMD)) is inoculated into each of the whey degradation medium of Blend A and the whey degradation medium of Blend B so that the viable cell count will be 2 to $4 \times 10^7$ cfu/ml. The Lactobacillus gasseri OLL2959 is a bacteriocin producer which can produce an effect of lowering blood uric acid level when taken in the body and therefore can be used as probiotics.

After the Lactobacillus gasseri OLL2959 is cultured until the pH of the whey degradation medium becomes 4.7, the Lactobacillus gasseri OLL2959 is neutrally cultured. Specifically, the Lactobacillus gasseri OLL2959 is cultured (neutral culture) for 21 hours at a temperature of 35 degrees while an aqueous potassium carbonate solution (40 WT %) is added to the whey degradation medium of Blend A, being stirred, so that the pH of the whey degradation medium of Blend A will be always in a range from 4.7 to 5. Similarly, the Lactobacillus gasseri OLL2959 is neutrally cultured while an aqueous potassium carbonate solution is added to the whey degradation medium of Blend B, being stirred, so that the pH of the whey degradation medium of Blend B will be always not lower than 5.5. The neutral culture is performed under the anaerobic condition where carbon dioxide is blown in the environment.

After the neutral culture, the number of viable cells of the Lactobacillus gasseri OLL2959 in each of the whey degradation medium (culture solution) of Blend A and that of Blend B is measured by pour plate culture using a BCP medium. FIG. 2 shows a result of the culture of Lactobacillus gasseri OLL2959 in Example 1. The viable cell count of the Lactobacillus gasseri OLL2959 in the whey degradation medium (culture solution) of Blend A is $1.1 \times 10^{10}$ cfu/ml, and the viable cell count of the Lactobacillus gasseri OLL2959 in the whey degradation medium (culture solution) of Blend B is $1.6 \times 10^{10}$ cfu/ml. There is not a large difference in the viable cell count of the Lactobacillus gasseri OLL2959 therein between the whey degradation medium (culture solution) of Blend A and that of Blend B even after the neutral culture.

By centrifuging the respective whey degradation media (culture solutions) of Blend A and Blend B (at acceleration of gravity of 6000 G), obtained are concentrated cell suspensions. The antibacterial activity of the concentrated cell suspension (hereinafter, referred to as "a concentrated cell suspension A") obtained from the whey degradation medium (culture solution) of Blend A and the antibacterial activity of the concentrated cell suspension (hereinafter, referred to as "a concentrated cell suspension B") obtained from the whey degradation medium (culture solution) of Blend B are measured by using such a method as discussed later.

As shown in FIG. 2, the antibacterial activity of the concentrated cell suspension A is lower than 200 AU (Arbitrary Unit) per 1 ml. Further, the antibacterial activity of the concentrated cell suspension A is lower than about 20 AU per $1 \times 10^9$ cfu. On the other hand, the antibacterial activity of the concentrated cell suspension B is 18000 AU per 1 ml. Further, the antibacterial activity of the concentrated cell suspension B is about 1100 AU per $1 \times 10^9$ cfu. In summary, the antibacterial activity per viable cell count of the concentrated cell suspension A obtained under the condition that the pH is in a range from 4.7 to 5 is about one sixtieth of the antibacterial activity per viable cell count of the concentrated cell suspension B obtained under the condition that the pH is not lower than 5.5.

Further, the Lactobacillus gasseri OLL2959 is neutrally cultured by using the whey degradation medium of Blend A while the pH of the whey degradation medium of Blend A is controlled to be not lower than 5. The result is that the viable cell count in the case where the neutral culture is performed under the condition that the pH is not lower than 5 is almost the same as that in the case where the neutral culture is performed under the condition that the pH is in a range from 4.7 to 5. The antibacterial activity per 1 ml in the case where the neutral culture is performed under the condition that the pH is not lower than 5 is higher than the antibacterial activity of the concentrated cell suspension A per 1 ml by one order of magnitude or more. Further, the Lactobacillus gasseri OLL2959 is cultured by using the whey degradation medium to which no emulsifier is added. The result is that the antibacterial activity per 1 ml in the case where the neutral culture of the Lactobacillus gasseri OLL2959 is performed under the condition that the pH is in a range from 4.7 to 5 is lower than the antibacterial activity per 1 ml in the case where the neutral culture is performed under the condition that the pH is not lower than 5 by one order of magnitude or more.

From these results, it is found that by neutrally culturing the Lactobacillus gasseri OLL2959 while maintaining the whey degradation medium at pH ranging from 4.7 to 5, it is possible to culture the Lactobacillus gasseri OLL2959 with high efficiency and control the antibacterial activity of the culture to be very low.

Further, the Lactobacillus gasseri OLL2959 is neutrally cultured by using the whey degradation medium of Blend A while the pH of the whey degradation medium of Blend A is controlled to be in a range from 4 to 4.7, to thereby obtain a concentrated cell suspension. The viable cell count in the case where the neutral culture is performed under the condition that the pH is in a range of 4 to 4.7 is slightly smaller than the viable cell count in the case where the neutral culture is performed under the condition that the pH is in a range of 4.7 to 5. The antibacterial activity of the concentrated cell suspension obtained by the neutral culture performed under the condition that the pH is in a range of 4 to 4.7 is almost the same as that of the concentrated cell suspension A. Thus, even when the neutral culture is performed under the condition that the pH is in a range of 4 to 4.7, it is possible to obtain the concentrated cell suspension of the Lactobacillus gasseri OLL2959 having very low antibacterial activity.

Example 2

FIG. 3 is a view showing the respective compositions of whey degradation media of Blend C and Blend D used in Example 2. First, discussion will be made on preparation of the whey degradation media of Blend C and Blend D. In the same procedure as in Example 1, the aqueous whey solution in which the whey protein is degraded is prepared. Then, with the blend ratios shown in FIG. 3, brewer's yeast extract, fish extract, sodium ascorbate, and ferrous sulfate are added to the aqueous whey solution.

After that, 0.025% by weight of Polysorbate 80 (Polyoxyethylene Sorbitan Monooleate, manufactured by NOF CORPORATION) and 0.025% by weight of Sun Soft 81S (Sorbitan Monooleate, manufactured by Taiyo Kagaku Co., Ltd.)

are added as emulsifiers to the aqueous whey solution to which the brewer's yeast extract and the like are added, to thereby prepare the whey degradation medium of Blend C. Further, 0.05% by weight of Sun Soft No. 25 (Polypropylene Glycol Monooleate, manufactured by Taiyo Kagaku Co., Ltd.) is added as an emulsifier to the aqueous whey solution to which the brewer's yeast extract and the like are added, to thereby prepare the whey degradation medium of Blend D.

Next, *Lactobacillus gasseri* OLL2959 is inoculated into each of the whey degradation medium of Blend C and the whey degradation medium of Blend D so that the viable cell count will be 2 to $4 \times 10^7$ cfu/ml. Like in Example 1, after the *Lactobacillus gasseri* OLL2959 is cultured until the pH of the whey degradation medium becomes 4.7, the *Lactobacillus gasseri* OLL2959 is neutrally cultured. Specifically, the *Lactobacillus gasseri* OLL2959 is neutrally cultured for 21 hours at a temperature of 35 degrees while an aqueous potassium carbonate solution (40 WT %) is added to each of the whey degradation media of Blend C and Blend D, being stirred, so that the pH of the whey degradation medium will be in a range from 4.7 to 5. The neutral culture is performed under the anaerobic condition where carbon dioxide is blown in the environment.

After the neutral culture, the number of viable cells of the *Lactobacillus gasseri* OLL2959 in each of the whey degradation media (culture solutions) of Blend C and Blend D is measured by the same method as in Example 1. FIG. 4 shows a result of the culture of *Lactobacillus gasseri* OLL2959 in Example 2. The viable cell count of the *Lactobacillus gasseri* OLL2959 in the whey degradation medium (culture solution) of Blend C is $1.6 \times 10^{10}$ cfu/ml, and the viable cell count of the *Lactobacillus gasseri* OLL2959 in the whey degradation medium (culture solution) of Blend D is $1.7 \times 10^{10}$ cfu/ml. There is no difference in the viable cell count of the *Lactobacillus gasseri* OLL2959 depending on the emulsifiers used for the whey degradation media (culture solutions).

By centrifugal separation, concentrated cell suspensions are separated from the whey degradation media (culture solutions) of Blend C and Blend D, respectively. The antibacterial activity of the concentrated cell suspension (hereinafter, referred to as "a concentrated cell suspension C") obtained from the whey degradation medium (culture solution) of Blend C and the antibacterial activity of the concentrated cell suspension (hereinafter, referred to as "a concentrated cell suspension D") obtained from the whey degradation medium (culture solution) of Blend D are measured by using the same method as in Example 1. The result is that the antibacterial activity of each of the concentrated cell suspensions C and D is lower than 200 AU per 1 nil. Further, the antibacterial activity of each of the concentrated cell suspensions C and D is lower than about 15 AU per $1 \times 10^9$ cfu.

The respective antibacterial activities of of the concentrated cell suspensions obtained by the neutrally culturing the whey degradation media (culture solutions) of Blend C and Blend D under the condition that the pH is in a range of 4 to 4.7 are almost the same as those of the concentrated cell suspensions C and D. The respective viable cell counts in the case where the whey degradation media (culture solutions) of Blend C and Blend D are neutrally cultured under the condition that the pH is in a range of 4 to 4.7 are slightly smaller than those in the case where the media are neutrally cultured under the condition that the pH is in a range of 4.7 to 5.

In the neutral culture using the whey degradation medium to which 0.025% by weight of Sun Soft No. 25 and 0.025% by weight of Sun Soft 81S are added as emulsifiers, the same result as that of Blend C is obtained.

From the experimental results in Examples 1 and 2, by using Polysorbate 80 and Sun Soft No. 25 as emulsifiers, it is possible to obtain the concentrated cell suspension having very low antibacterial activity. Further, in the case where Polysorbate 80 and Sun Soft No. 25 are used as emulsifiers, even by using the other emulsifier with these emulsifiers, it is possible to obtain the concentrated cell suspension having very low antibacterial activity.

(Method for Measuring Antibacterial Activity)

Next, discussion will be made on a method for measuring the antibacterial activity of the concentrated cell suspension, taking the concentrated cell suspension A as an example. The respective antibacterial activities of the concentrated cell suspensions B, C, and D are also measured by the same method.

An MRS medium (manufactured by Becton, Dickinson and Company) currently on the market is used. A test medium is prepared by adding 0.1% volume/volume (v/v) of indicator bacterium, based on the MRS medium. As the indicator bacterium, used is *Lactobacillus delbrueckii* subsp. *bulgaricus* ATCC11842 (type strain).

The frozen and stored concentrated cell suspension A is kept in a hot water bath for 5 minutes, and then a 1% (v/v) aqueous solution of the concentrated cell suspension A is prepared. The aqueous solution of the concentrated cell suspension A is progressively diluted by 2-fold and a plurality of diluted solutions of the concentrated cell suspension A which are different in the level of dilution rate are obtained. The levels of dilution rate ranges from 8 to 12. The $2^8$-fold to $2^{12}$-fold diluted solutions of the concentrated cell suspension A are thereby prepared. These diluted solutions are added to the test media, respectively, and then the test media to which the $2^8$-fold to $2^{12}$-fold diluted solutions are added are anaerobically cultured by using AnaeroPack-Anaero (manufactured by Mitsubishi Gas Chemical Company, Inc.) for 24 hours at a temperature of 37 degrees.

After the anaerobic culture, checked is the maximum level (n) of dilution rate at which no indicator bacterium is grown. Then, on the basis of the maximum level (n) of dilution rate and the concentration (0.01:1%) of the aqueous solution of the concentrated cell suspension, the antibacterial activity (AU) of the concentrated cell suspension A is obtained. The antibacterial activity can be obtained on the basis of the following formula.

antibacterial activity (AU)=the maximum level (n) of dilution rate/the concentration (0.01) of the aqueous solution of the concentrated cell suspension Hereafter, discussion will be made on a method for producing yogurt to which each of the concentrated cell suspensions A to C is added, as an Example of the method for producing fermented milk in accordance with the present invention.

Example 3

FIG. 5 is a view showing the respective compositions of four types of yogurt mixes used in Example 3. First, discussion will be made on preparation of yogurt mixes of Blends E to H. Yogurt mixes of Blends E to H are each prepared by mixing 14.10% by weight of skimmed milk powder (manufactured by Meiji Dairies Corporation), 0.93% by weight of unsalted butter (manufactured by Meiji Dairies Corporation), and water, based on the total weight of the yogurt mix. The blend ratios of water are 82.97 WT % in Blend E and 82.87 WT % in Blends F to H.

The yogurt mixes of Blends E to H are homogenized and disinfected in the same manner as conventionally done, and then the yogurt mixes of Blends E to H are cooled to a temperature of about 40 degrees. After the cooling, the yogurt mixes of Blends E to H are inoculated with 2.00% by weight of lactic acid bacterium starter. As the lactic acid bacterium starter, used is the lactic acid bacterium separated from Meiji Bulgaria Yogurt (manufactured by Meiji Dairies Corporation).

The yogurt mix of Blend F is inoculated with 0.10% by weight of the concentrated cell suspension A. The yogurt mix of Blend G is inoculated with 0.10% by weight of the concentrated cell suspension B. The yogurt mix of Blend H is inoculated with 0.10% by weight of the concentrated cell suspension C. The yogurt mix of Blend E is inoculated with no concentrated cell suspension. Then, the yogurt mixes are each fermented at a temperature of 40 degrees until the lactate concentration becomes about 1.20%, to thereby produce yogurts. At that time, the time (fermentation time) needed for the lactate concentration of each of the yogurt mixes to become 1.20% is measured.

The fermentation time for the yogurt mix of Blend E inoculated with no concentrated cell suspension and the respective yogurt mixes of Blend F and H inoculated with the concentrated cell suspensions A and C is 5 hours. From this result, it is found that there arises no delay in the fermentation of the yogurt mixes (Blends F and H) inoculated with the concentrated cell suspensions A and C each having low antibacterial activity.

On the other hand, the fermentation time for the yogurt mix (Blend G) inoculated with the concentrated cell suspension B having high antibacterial activity is 7 hours. In summary, there arises a delay in the fermentation of the yogurt mix of Blend G. It can be understood that by adding the concentrated cell suspension B having high antibacterial activity to the yogurt mix, the bacteriocin contained in the concentrated cell suspension B retards the action of the lactic acid bacterium starter in the yogurt mix of Blend G.

Thus, by adding the culture (the concentrated cell suspension A or C) obtained by performing the neutral culture while maintaining the whey degradation medium at pH of not lower than 4.7 and lower than 5 to the yogurt mix, it is possible to produce yogurt to which the bacteriocin producer is added with high efficiency in almost the same fermentation time as in the case of producing the conventional yogurt. Therefore, even when the bacteriocin producer is used as probiotics, the same manufacturing process as that for the conventional yogurt can be used.

While the invention has been shown and described in detail, the foregoing description is in all aspects illustrative and not restrictive. It is therefore understood that numerous modifications and variations can be devised without departing from the scope of the invention.

The invention claimed is:

1. A method comprising:
 a culture solution preparation step of preparing a culture solution containing whey degraded by a proteolytic enzyme; and
 a culture step of
  inoculating bacteriocin-producing, lactic acid bacteria, which belongs to *Lactobacillus gasseri*, into said culture solution, and
  culturing said bacteriocin-producing, lactic acid bacteria until a pH of said culture solution inoculated with said bacteriocin-producing, lactic acid bacteria becomes lower than 5, and then culturing said bacteriocin-producing, lactic acid bacteria while maintaining the pH of said culture solution inoculated with said bacteriocin-producing, lactic acid bacteria to be lower than 5 and not lower than 4.7 by adding an alkaline solution to said culture solution inoculated with said bacteriocin-producing, lactic acid bacteria.

2. The method according to claim 1, further comprising:
 a separation step of separating a concentrated cell suspension containing said bacteriocin-producing, lactic acid bacteria from said culture solution in a concentrated form to provide said concentrated cell suspension.

3. The method according to claim 1, wherein said culture solution preparation step includes:
 an emulsifier addition step of adding an emulsifier to said culture solution.

4. The method according to claim 3, wherein said emulsifier contains either propylene glycol monooleate or polyoxyethylene sorbitan monooleate.

5. The method according to claim 1, wherein in said culture solution preparation step, said proteolytic enzyme is added to an aqueous whey solution prepared by mixing whey and water.

6. The method according to claim 1, further comprising:
 an add step of adding into a yogurt mix, a culture of said bacteriocin-producing, lactic acid bacteria produced by said culture step, and a starter, wherein the yogurt mix is a raw material milk for forming fermented milk; and
 a ferment step of fermenting said yogurt mix which includes the culture of said bacteriocin-producing, lactic acid bacteria and the starter,
 wherein the culture of said bacteriocin-producing, lactic acid bacteria is produced by said culture step which is done separately from said ferment step.

7. The method according to claim 1, wherein the bacteriocin-producing, lactic acid bacteria belongs to *Lactobacillus gasseri* OLL2959.

8. A method comprising:
 a culture solution preparation step of preparing a culture solution containing whey degraded by a proteolytic enzyme;
 a culture step of
  inoculating bacteriocin-producing, lactic acid bacteria, which belongs to *Lactobacillus gasseri*, into said culture solution,
  culturing said bacteriocin-producing, lactic acid bacteria until a pH of said culture solution inoculated with said bacteriocin-producing, lactic acid bacteria becomes lower than 5,
  after the pH becomes lower than 5, culturing said bacteriocin-producing, lactic acid bacteria while maintaining the pH of said culture solution inoculated with said bacteriocin-producing, lactic acid bacteria to be lower than 5 and not lower than 4.7 by adding an alkaline solution to said culture solution inoculated with said bacteriocin-producing, lactic acid bacteria;
 an add step of adding into a yogurt mix, a culture of said bacteriocin-producing, lactic acid bacteria produced by said culture step, and a starter, wherein the yogurt mix is a raw material milk for forming fermented milk; and
 a ferment step of fermenting said yogurt mix which includes the culture of said bacteriocin-producing, lactic acid bacteria and the starter,
 wherein the culture of said bacteriocin-producing, lactic acid bacteria is produced by said culture step which is done separately from said ferment step.

9. The method according to claim 8, further comprising:
 a separation step of separating a concentrated cell suspension containing said bacteriocin-producing, lactic acid bacteria from said culture solution in a concentrated form to provide said concentrated cell suspension.

10. The method according to claim 8, wherein said culture solution preparation step includes:
    an emulsifier addition step of adding an emulsifier to said culture solution.

11. The method according to claim 10, wherein said emulsifier contains either propylene glycol monooleate or polyoxyethylene sorbitan monooleate.

12. The method according to claim 8, wherein in said culture solution preparation step, said proteolytic enzyme is added to an aqueous whey solution prepared by mixing whey and water.

13. The method according to claim 8, wherein the bacteriocin-producing, lactic acid bacteria belongs to *Lactobacillus gasseri* OLL2959.

* * * * *